(12) United States Patent
Adams

(10) Patent No.: US 7,985,205 B2
(45) Date of Patent: Jul. 26, 2011

(54) MEDICAL CATHETER EXTERNAL BOLSTER HAVING STRAIN RELIEF MEMBER

(75) Inventor: Mark L. Adams, Sandy, UT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 385 days.

(21) Appl. No.: 11/226,807

(22) Filed: Sep. 14, 2005

(65) Prior Publication Data
US 2007/0078441 A1 Apr. 5, 2007

(51) Int. Cl.
*A61M 5/32* (2006.01)
*A61M 25/00* (2006.01)

(52) U.S. Cl. .................. 604/174; 604/523
(58) Field of Classification Search .............. 604/174, 604/177, 178, 179, 180
See application file for complete search history.

(56) References Cited

U.S. PATENT DOCUMENTS

| | | | | |
|---|---|---|---|---|
| 1,998,225 | A * | 4/1935 | Dow | 604/174 |
| 4,645,492 | A * | 2/1987 | Weeks | 604/174 |
| 4,666,433 | A * | 5/1987 | Parks | 604/178 |
| 4,834,712 | A * | 5/1989 | Quinn et al. | 604/175 |
| 4,861,334 | A | 8/1989 | Nawaz | |
| 4,900,306 | A | 2/1990 | Quinn et al. | |
| 5,112,310 | A | 5/1992 | Grobe | |
| 5,167,627 | A | 12/1992 | Clegg et al. | |
| 5,267,968 | A * | 12/1993 | Russo | 604/174 |
| 5,391,159 | A | 2/1995 | Hirsch et al. | |
| 5,451,212 | A * | 9/1995 | Andersen | 604/174 |
| 5,484,420 | A * | 1/1996 | Russo | 604/178 |
| 5,865,816 | A | 2/1999 | Quinn | |
| 6,036,673 | A * | 3/2000 | Quinn | 604/178 |
| 6,066,112 | A | 5/2000 | Quinn | |
| 6,471,676 | B1 | 10/2002 | DeLegge | |
| 6,482,183 | B1 * | 11/2002 | Pausch et al. | 604/174 |
| 6,641,575 | B1 * | 11/2003 | Lonky | 604/540 |
| 7,147,620 | B2 * | 12/2006 | Kessler et al. | 604/104 |
| 2003/0187424 | A1 | 10/2003 | Chu et al. | |

FOREIGN PATENT DOCUMENTS
WO WO 94/08648 A1 4/1994
WO WO 95/15781 A1 6/1995
* cited by examiner

*Primary Examiner* — Theodore J Stigell
*Assistant Examiner* — William Carpenter
(74) *Attorney, Agent, or Firm* — Kenyon & Kenyon LLP

(57) ABSTRACT

An external bolster for a medical catheter, the external bolster comprising an integral strain relief member for diminishing the effect of an externally-directed force applied to the medical catheter. In a preferred embodiment, the external bolster is a flexible, unitary member comprising a lower portion and an upper portion. The lower portion comprises an annular base, the base having a top surface, a bottom surface and a central opening. A plurality of spaced apart feet extend downwardly from the bottom surface of the base. A sleeve extends upwardly from the top surface of the base in alignment with the central opening, the sleeve and the central opening jointly defining a bore of uniform cross-section. The upper portion comprises an elbow-shaped tubular member having a vertical portion, a horizontal portion and a longitudinal lumen. The vertical portion of the tubular member is disposed on top of the sleeve, with its lumen aligned with the bore. The upper portion also includes a tether for maintaining the tubular member in a bent state, the tether having a first end secured to the horizontal portion and a second end secured to the vertical portion.

24 Claims, 9 Drawing Sheets

MEDICAL CATHETER EXTERNAL BOLSTER HAVING STRAIN RELIEF MEMBER

BACKGROUND OF THE INVENTION

The present invention relates generally to external bolsters of the type used to retain an implanted medical catheter in the body of a patient and relates more particularly to external bolsters of the aforementioned type that include means for relieving strain applied to the medical catheter.

Certain patients are unable to take food and/or medications transorally due to an inability to swallow. Such an inability to swallow may be due to a variety of reasons, such as esophageal cancer, neurological impairment and the like. Although the intravenous administration of food and/or medications to such patients may be a viable short-term approach, it is not well-suited for the long-term. Accordingly, the most common approach to the long-term feeding of such patients involves gastrostomy, i.e., the creation of a feeding tract or stoma between the stomach and the upper abdominal wall. (A less common approach involves jejunostomy, i.e., the creating of a feeding tract or stoma leading into the patient's jejunum.) Feeding is then typically performed by administering food through a catheter or feeding tube that has been inserted into the feeding tract, with one end of the feeding tube extending into the stomach and being retained therein by an internal anchor or bolster and the other end of the feeding tube extending through the abdominal wall and terminating outside of the patient.

Although gastrostomies were first performed surgically, most gastrostomies are now performed using percutaneous endoscopy and result in the implantation of a feeding tube/internal bolster assembly (also commonly referred to as a percutaneous endoscopic gastrostomy (PEG) device) in the patient. Two of the more common techniques for implanting a PEG device in a patient are "the push method" (also known as "the Sacks-Vine method") and "the pull method" (also known as "the Gauderer-Ponsky method"). Information regarding the foregoing two methods may be found in the following patents, all of which are incorporated herein by reference: U.S. Pat. No. 5,391,159, inventors Hirsch et al., which issued Feb. 21, 1995; U.S. Pat. No. 5,167,627, inventors Clegg et al., which issued Dec. 1, 1992; U.S. Pat. No. 5,112,310, inventor Grobe, which issued May 12, 1992; U.S. Pat. No. 4,900,306, inventors Quinn et al., which issued Feb. 13, 1990; and U.S. Pat. No. 4,861,334, inventor Nawaz, which issued Aug. 29, 1989.

According to the push method, one end of an endoscope is intubated (i.e., inserted) into a patient's mouth and is passed through the esophagus into the stomach. After distension of the stomach by inflation, an entry site on the abdomen is identified using the endoscope for transillumination, and an incision is made by passing the tip of a needle coupled to an outer cannula through the abdominal and stomach walls and into the stomach. One end of the outer cannula remains outside of the body and acts as a stop to prevent the external end of the needle from falling into the stomach. A snare is inserted into the stomach via the endoscope and is looped over the inserted end of the needle. The snare is then "walked" up the needle until the outer cannula is snared. The snared cannula is then pulled externally to tack the cannula to the stomach and, in turn, to secure the stomach wall to the abdominal wall. The needle is then removed while keeping the cannula in place. A first end of a flexible guidewire is then passed through the cannula and into the stomach where it is grasped by the snare, the second end of the guidewire remaining external to the patient. The endoscope and the snare are then withdrawn from the mouth of the patient to deliver the first end of the guidewire.

A push-type catheter implanting assembly is then inserted over the first end of the guidewire and is pushed over the guidewire towards its second end. The push-type catheter implanting assembly typically comprises a gastrostomy feeding tube, the gastrostomy feeding tube having a dome-shaped internal bolster disposed at its trailing end and having a tubular dilator serially connected to its leading end. The gastrostomy feeding tube and the internal bolster are typically made of a soft, biocompatible material, like silicone rubber, and may form a unitary structure. The dilator, which tapers in outer diameter from its trailing end to its leading end, is typically made of polyethylene or a like material which is stiffer than silicone but which still possesses some flexibility. Advancement of the push-type catheter implanting assembly over the guidewire continues until the front end of the dilator reaches the cannula and pushes the cannula out through the abdominal wall of the patient. The front end of the dilator is then pulled through the abdominal wall until the front end of the gastrostomy feeding tube emerges from the abdomen and, thereafter, the internal bolster at the rear end of the gastrostomy feeding tube engages the stomach wall. The guidewire is then removed from the patient. The clinician then re-intubates the patient with the endoscope and uses an optical channel in the endoscope to inspect whether the internal bolster is properly seated in the stomach.

If the internal bolster is properly placed against the stomach wall, a length of the externally-extending portion of the implanted gastrostomy feeding tube is then typically cut and removed from the implanted tube to reduce the externally-extending portion of the tube to a desired length (typically about 4-6 inches). (The removal of the leading end of the gastrostomy feeding tube also results in the removal of the dilator, which is connected thereto.)

The pull method is similar in some respects to the above-described push method, the pull method differing from the push method in that, after the cannula is snared and the needle is removed therefrom, a first end of a suture is inserted through the cannula and into the stomach where it is grasped by the snare, the second end of the suture remaining external to the patient. The endoscope and the snare are then withdrawn from the mouth of the patient to deliver the first end of the suture. The first end of the suture is then coupled to the leading end of a pull-type catheter implanting assembly, the pull-type catheter implanting assembly typically comprising a gastrostomy feeding tube having an internal bolster at its trailing end and a plastic fitting at its leading end. The plastic fitting typically has a barbed rear portion mounted within the leading end of the feeding tube and a conical front portion that serves as a dilator, said conical front portion tapering in diameter from the leading end of the feeding tube to a front tip. A wire loop is fixed to the front tip of the plastic fitting, the first end of the suture being tied to the wire loop. Using the second end of the suture, the pull-type catheter implanting assembly is then pulled retrograde through the patient until the gastrostomy feeding tube emerges from the abdomen of the patient and the internal bolster engages the stomach wall of the patient. Next, as is the case in the push method, the clinician then re-intubates the patient with the endoscope in order to visually inspect the placement of the internal bolster within the stomach. If the bolster is properly seated in the stomach, the externally-extending portion of the implanted gastrostomy feeding tube is then typically cut to a desired length.

Regardless of whether a PEG device is implanted by the above-described push method, by the above-described pull method or by another method, complications may arise if the PEG device is positioned too far internally within the patient. More specifically, if the trailing (i.e., internal) end of the PEG device, especially the internal bolster, is positioned too far internally within the patient, the PEG device can cause blockages in the patient's stomach or otherwise interfere with stomach function. Furthermore, if the trailing end of the PEG device is positioned too far internally within the patient, the leading (i.e,. external) end of the PEG may be drawn entirely into the patient's stomach, possibly causing great harm to the patient.

For the above reasons, it is customary to use an externally located device, typically referred to in the art as an external bolster, to retain the external portion of the PEG device outside of the patient. An external bolster typically comprises an enlarged annular member that is shaped to include a central bore through which the external portion of the PEG device may be inserted. Preferably, the central bore is appropriately dimensioned to provide an interference (i.e., frictional) fit between the external bolster and the feeding tube fed therethrough. In use, the leading (i.e., external) end of the implanted PEG device is inserted through the central bore in the external bolster as far as possible. Due to the significant interference fit between the outer diameter of the feeding tube and the inner diameter of the external bolster, forceps or the like may be used to facilitate the insertion of the leading end of the feeding tube through the central bore of the external bolster. The feeding tube is preferably advanced through the central bore until the bottom surface of the external bolster is drawn into direct contact with the patient's skin in the area surrounding the wound site. Positioned in this manner, the external bolster effectively anchors the implanted PEG device in its proper position and prevents any migration of the device into the patient's stomach. Although not needed in all cases, it may be desirable in certain instances for the external bolster to be sutured to the patient's skin.

Although external bolsters of the type described above function satisfactorily to prevent the external end of an implanted PEG device from being withdrawn into a patient's stomach, most such external bolsters do not additionally provide strain relief to dissipate the effect of an externally-directed pulling force applied to the PEG device. Such strain relief is highly desirable as it has been found that certain patients (e.g., patients suffering from dementia or Alzheimer's disease) often knowingly or unknowingly attempt to remove implanted PEG devices from their bodies by pulling on the external end of the PEG device. As can be readily be appreciated, the application of a sufficiently great pulling force on the external end of an implanted PEG device can ultimately result in, among other things, the ill-advised removal of the PEG device from the patient and/or significant injury to the patient at the site of implantation (e.g., tearing of sutures, damage to the stoma, etc.).

In response to the above problem, certain external bolsters have been devised that provide strain relief to an implanted feeding tube. For example, in U.S. Pat. No. 6,471,676, inventor DeLegge, which issued Oct. 29, 2002, and which is incorporated herein by reference, a catheter retention device is disclosed that is designed to relieve strain caused by physical force exerted against the catheter. The retention device, which is unitary in design and constructed out of a flexible material, such as silicone or thermoplastic rubber, includes a base component which supports first and second substantially cylindrical retention ring housing components, the second retention ring housing component being positioned on the base such that the axis of its centrally disposed bore is out of axial alignment with the centrally disposed bore for the first retention ring housing component. In use, the portion of an implanted feeding tube which exits the patient's body is first passed through a bore formed in the base component. The feeding tube is then curved at approximately a ninety degree (90°) angle and is threaded through the central bore of the first retention ring housing component. The feeding tube is then looped around at an angle of approximately two hundred-seventy degrees (270°), preferably on a plane parallel to the base component so as to be threadably insertable through the central bore of the second retention ring housing component whose axis is perpendicular to that of the bore of the first retention ring housing component. Once the feeding tube is fed through the base component and both retention ring housing components as described above, the base is attached to the skin of the patient using any one of a number of attachment means or methods known in the art such as sutures, staples, adhesive tapes or liquid adhesives.

SUMMARY OF THE INVENTION

It is an object of the present invention to provide a novel external bolster of the type suitable for use in retaining within a patient an implanted medical catheter, such as a gastrostomy feeding tube.

It is another object of the present invention to provide an external bolster as described above that addresses at least some of the shortcomings present in connection with existing external bolsters.

It is still another object of the present invention to provide an external bolster as described above that is adapted to relieve strain applied to an implanted medical catheter secured thereto.

It is yet still another object of the present invention to provide an external bolster that is inexpensive to manufacture and is easy to use.

Therefore, according to one feature of the present invention, there is provided an external bolster for a medical catheter implanted in a patient at an insertion site, said external bolster comprising (a) a base, said base being enlarged relative to the insertion site of the medical catheter, said base having an opening through which the medical catheter may be inserted; and (b) a tubular strain relief member, said tubular strain relief member being coupled to said base and through which the medical catheter may be inserted, said tubular strain relief member having a first arm, a second arm and a longitudinal lumen, said longitudinal lumen extending through said first and second arms, said first arm and said second arm being positioned relative to one another at an angle, said angle being greater than 0 degrees and less than 180 degrees.

According to another feature of the present invention, there is provided an external bolster for a medical catheter implanted in a patient at an insertion site, said external bolster comprising (a) a base, said base being enlarged relative to the insertion site of the medical catheter, said base having an opening through which the medical catheter may be inserted; and (b) a tubular strain relief member, said tubular strain relief member being coupled to said base and through which the medical catheter may be inserted, said tubular strain relief member having a longitudinal lumen, said longitudinal lumen having a first portion and a second portion, said first portion and said second portion being positioned relative to one another at an angle, said angle being greater than 0 degrees and less than 180 degrees.

According to yet another feature of the present invention, there is provided the combination of (a) a medical catheter, said medical catheter including a first end, a second end, and a longitudinal lumen; and (b) a strain relief device, said strain relief device comprising a flexible tubular member including a first arm terminating in a first end, a second arm terminating in a second end, said first arm and said second arm being disposed relative to one another at an angle greater than 0 degrees and less than 180 degrees, said medical catheter being inserted into said strain relief device, with said first end of said medical catheter extending beyond said first end of said first arm and said second end of said medical catheter extending beyond said second end of said second arm.

According to still yet another feature of the present invention, there is provided a strain relief device for a medical catheter, said strain relief device comprising (a) a flexible tubular member dimensioned to receive a medical catheter, and (b) a tether coupled to said flexible tubular member at a pair of locations, said tether retaining said flexible tubular member in a bent state.

For purposes of the present specification and claims, various relational terms like "top," "bottom," "proximal," "distal," "upper," "lower," "front," and "rear" are used to describe the present invention when said invention is positioned in or viewed from a given orientation. It is to be understood that, by altering the orientation of the invention, certain relational terms may need to be adjusted accordingly.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration certain embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts.

DETAILED DESCRIPTION OF PREFERRED EMBODIMENTS

Figure 1A:
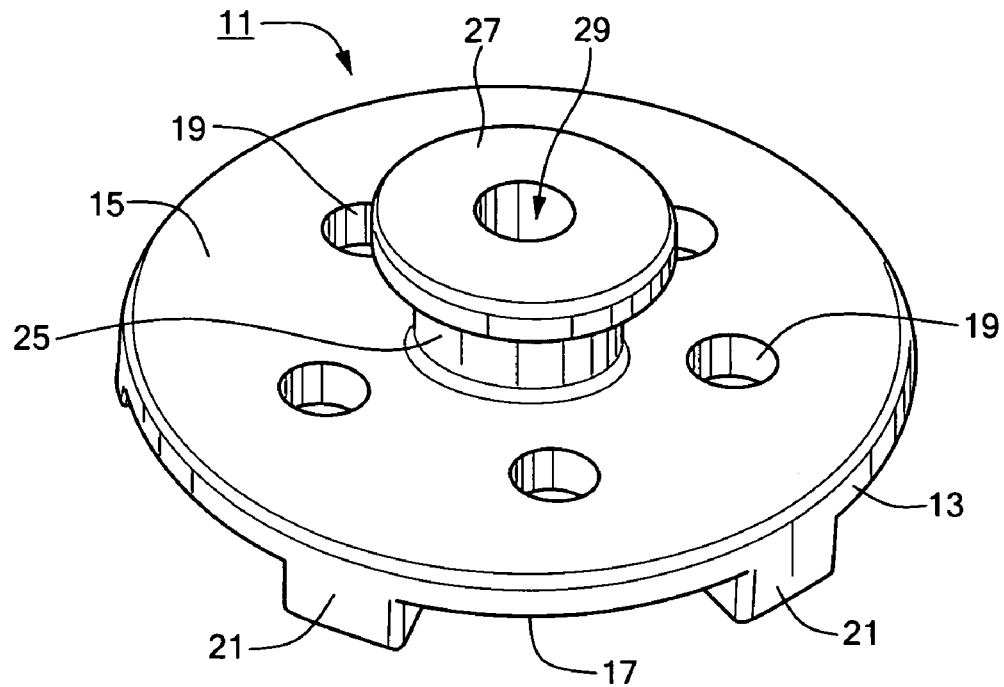
FIGS. 1(a) and 1(b) are top perspective and section views, respectively, of a conventional external bolster of the type adapted for use with an implanted PEG device to prevent the inward migration of the PEG device into a patient.
Figure 1B:
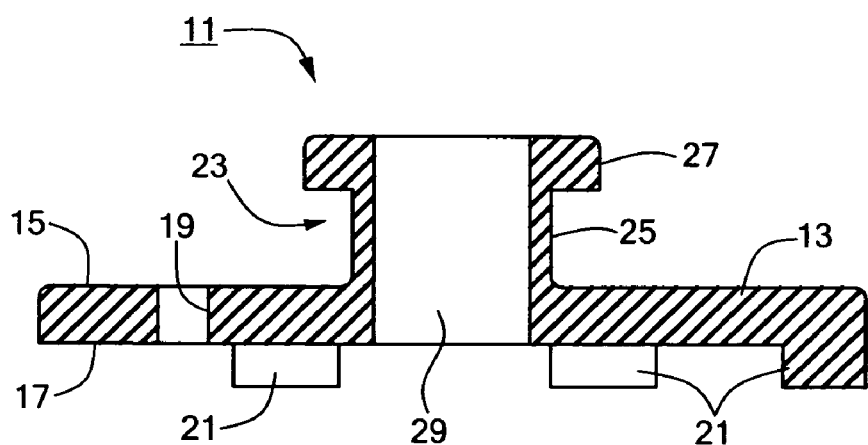

Referring now to FIGS. 1(a) and 1(b), there are shown top perspective and section views, respectively, of a conventional external bolster of the type designed to prevent an implanted medical catheter, such as a PEG device, from being drawn into a patient's body, the conventional external bolster being represented generally by reference numeral 11.

Bolster 11, which is a unitary member typically made of silicone using conventional molding techniques, includes an enlarged annular base 13 having a substantially flat top surface 15 and a substantially flat bottom surface 17. A plurality of air holes 19 are provided in base 13 in a spaced apart relationship. Each air hole 19 is generally circular in lateral cross-section and extends through base 13 from top surface 15 to bottom surface 17. Together, air holes 19 facilitate the aeration of a stoma site, as will be described further below.

A plurality of feet 21 are formed on bottom surface 17 of base 13 along its outer periphery in a spaced apart relationship. Each foot 21 is in the shape of a block which is generally rectangular in lateral cross-section. With bolster 11 properly mounted on a feeding tube, feet 21 are designed to contact the skin of a patient in the area surrounding a stoma site. In this manner, feet 21 serve (i) to keep bolster 11 out of contact with the stoma site and to minimize the surface area of bolster 11 that contacts the patient's skin, thereby limiting any irritation to the patient resulting from contact with bolster 11; and (ii) to elevate bottom surface 17 of base 13 away from the patient's skin, thereby promoting the aeration of the stoma site and reducing the risk of bacterial infection.

A short sleeve 23 is centrally located on base 13 and extends orthogonally upwardly from top surface 15 of base 13. Sleeve 23 includes a lower neck portion 25 of smaller outer diameter and an upper flange portion 27 of greater outer diameter. Sleeve 23 and base 13 jointly define an elongated central bore 29 which is of a uniform circular shape in lateral cross-section therethrough. Central bore 29 is sized and shaped to receive a conventional feeding tube. Preferably, central bore 29 is appropriately dimensioned so that a strong interference (i.e., friction) fit is established between external bolster 11 and a feeding tube which is inserted through central bore 29. In this manner, external bolster 11 can be secured tightly to a feeding tube, the enlarged size of bolster 11 acting as a stop, or barrier, for limiting the inward migration of the feeding tube into the patient.

Figure 2:
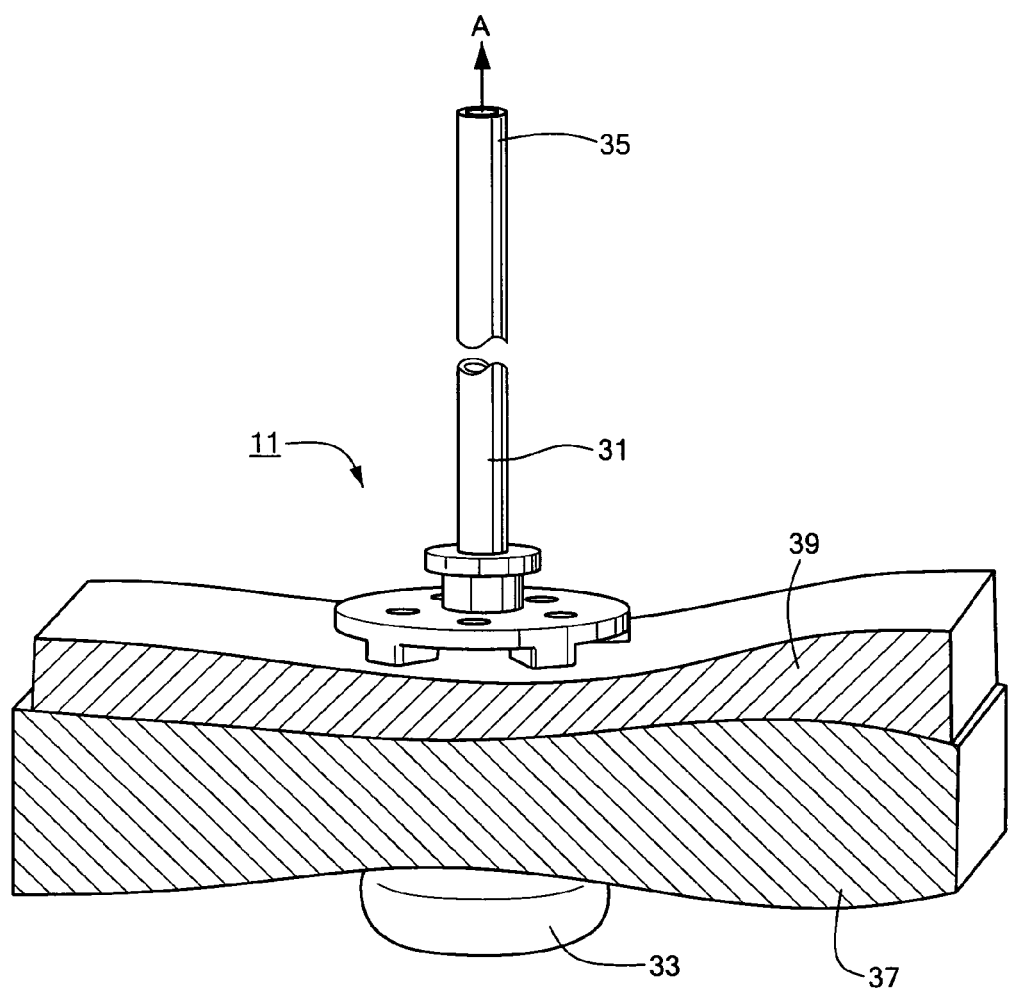
FIG. 2 is a perspective view of the external bolster shown in FIGS. 1(a) and 1(b), the external bolster being mounted on a PEG device, the PEG device being shown implanted in the body of a patient, the patient's body being shown in fragmentary section.

Referring now to FIG. 2, external bolster 11 is shown mounted on an implanted PEG device to prevent the implanted PEG device from migrating into a patient's stomach. As can be seen, the implanted PEG device comprises a feeding tube 31, feeding tube 31 having an internal end 33 and an external end 35, internal end 33 being shaped to define a dome-shaped internal bolster. As shown, the implanted PEG device is being pulled externally (i.e., away from the patient or in the direction of arrow A) so that internal end 33 engages the stomach wall 37 of a patient and presses stomach wall 37 against the abdominal wall 39 of the patient. External bolster 11, which is inserted over external end 35 of tube 31 and slid down into contact with abdominal wall 39, is oriented so that feet 21 are pressed against abdominal wall 39 and so that sleeve 23 extends away from abdominal wall 39. If necessary, forceps or the like may be used to facilitate the insertion of external end 35 of feeding tube 31 through bore 29 of bolster 11.

As noted above, central bore 29 is dimensioned so as to create a significant interference fit between feeding tube 31 and bolster 11. As a result, with feet 21 uniformly disposed in contact against the patient's skin outside the area of the stoma, external bolster 11 effectively functions as an anchor to prevent feeding tube 31 from inwardly migrating into the patient's stomach. In addition, feet 21 serve to space bottom surface 17 of base 13 substantially away from the patient's skin in order to permit the circulation of air around the stoma site. Air holes 19 increase the degree of air circulation around the stoma site and may be used, if desired, to suture bolster 11 to the patient.

It should be noted that external bolster 11 is not limited to use with a PEG device, but rather, may be used with any type of medical catheter (e.g., a jejunostomy feeding tube, a drainage tube, etc.).

As noted above, it has been found that certain patients often intentionally pull on the externally-extending portion of an implanted PEG device in a misguided attempt to remove the PEG device from their bodies. In addition, it is not uncommon for medical care providers or for the patients, themselves, to accidentally pull on the externally-extending portion of an implanted PEG device while performing everyday activities. Because external bolster 11 provides no strain relief (i.e., no diminishment of the externally-directed force transmitted to the PEG device) when feeding tube 31 is pulled externally, this force can ultimately result in, among other things, the dislodgement of the PEG device and/or significant injury to the patient (e.g., tearing of stoma, etc.).

In addition, although the PEG device of FIG. 2 is shown with feeding tube 31 being pulled directly upright, it should be understood that, when no external force is applied to the PEG device, the external portion of feeding tube 31 will go limp and rest upon the top surface of abdominal wall 39. As can readily be appreciated, such contact between the external portion of feeding tube 31 and abdominal wall 39 may, over time, cause irritation to the patient's skin, leading to ulcers or the like.

Figure 3A:
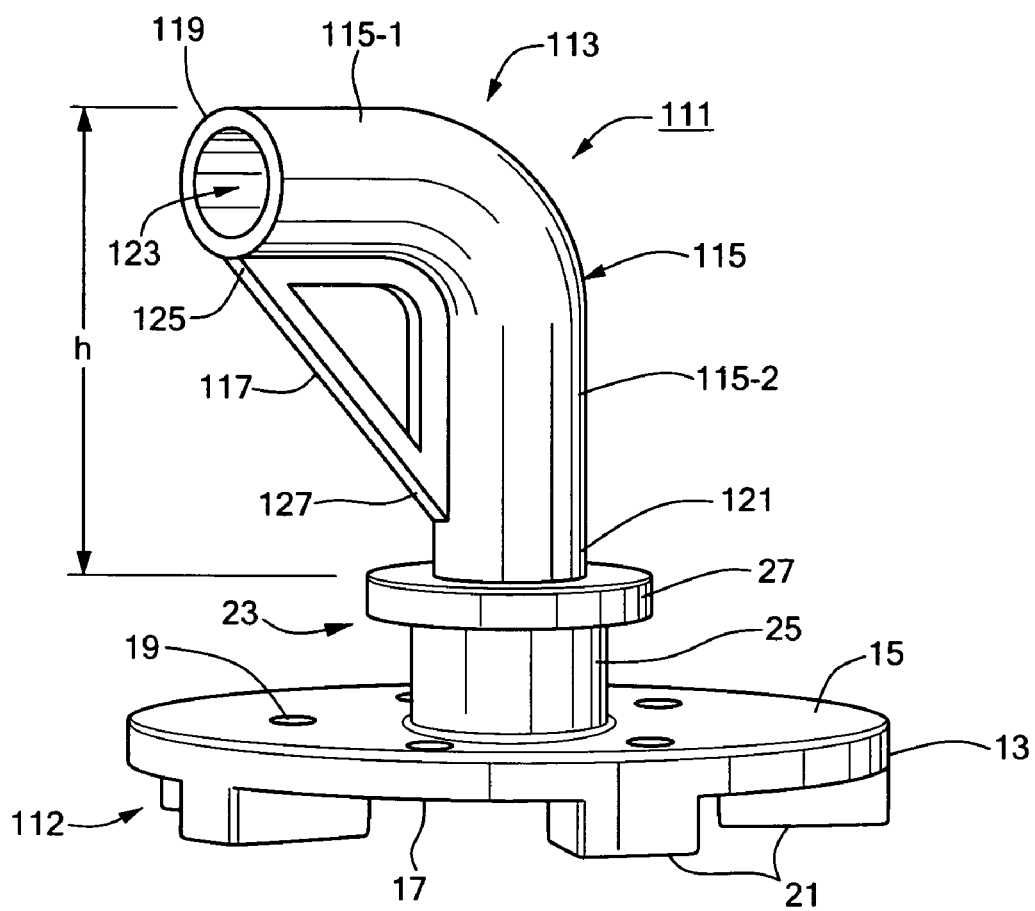
FIGS. 3(a) and 3(b) are top perspective and section views, respectively, of a first embodiment of an external bolster constructed according to the teachings of the present invention.
Figure 3B:
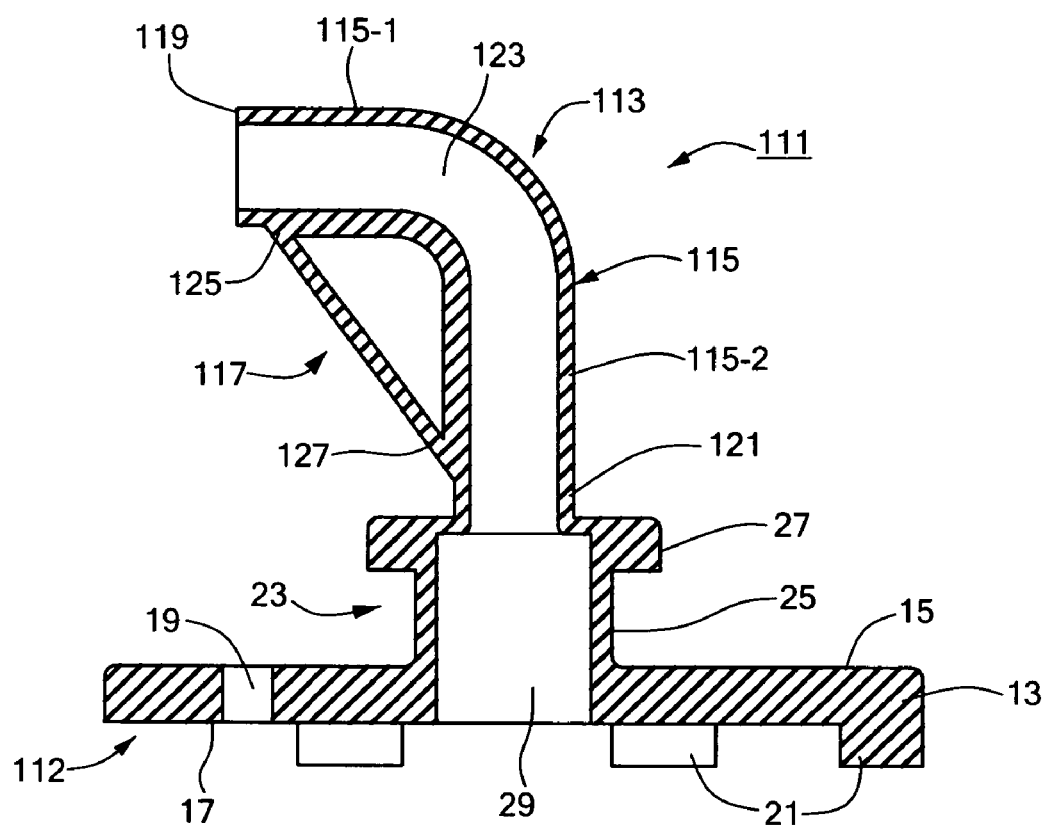

Referring now to FIGS. 3(a) and 3(b), there are shown perspective and section views, respectively, of a first embodiment of an external bolster constructed according to the teachings of the present invention, said external bolster being represented generally by reference numeral 111. As will be described below in further detail, bolster 111 is adapted to be slidably mounted over an implanted medical catheter, such as a PEG device, in order to absorb (i.e., to diminish or to relieve) undesirable externally-directed forces that are exerted on the externally-extending portion of said PEG device.

Bolster 111, which is preferably a molded unitary structure made of a flexible material, such as a 40A durometer silicone, comprises a lower portion 112 and an upper portion 113. Lower portion 112 is identical in structure to bolster 11. Upper portion 113 comprises an elbow-shaped (i.e., 90 degree) tubular strain relief member 115 and a tether 117. Tubular member 115 is shaped to include a first arm 115-1 terminating in a first end 119, a second arm 115-2 terminating in a second end 121, and a longitudinal lumen 123. As will be discussed below, tubular member 115 has a height h of approximately 1-2 inches; in this manner, a substantial length of the externally-extending portion of an implanted catheter extending through bolster 111 is elevated relative to a patient's skin. Second end 121 of tubular member 115 is disposed at the upper end of sleeve 23, with lumen 123 aligned with bore 29. Lumen 123 preferably has a diameter equal to that of bore 29 so that a strong interference (i.e., friction) fit may be established between tubular member 115 and a catheter inserted through lumen 123. As will be discussed below, because tubular member 115 is bent at a 90 degree angle, the externally-extending portion of an implanted catheter that is inserted through tubular member 115 extends perpendicularly relative to the insertion angle of the implanted catheter in the patient. As a result, an externally-directed pulling force applied to the externally-extending portion of the implanted catheter is substantially reduced in magnitude along the insertion angle of the implanted catheter.

Tether 117, which causes tubular member 115 to be held in a bent shape, is preferably a thin strengthening member having a first end 125 and a second end 127. First end 125 of tether 117 is secured to tubular member 115 at a point proximate to first end 119 and second end 127 of tether 117 is secured to tubular member 115 at a point proximate to second end 121.

To facilitate the threading of an implanted feeding tube through bolster 111, one or both of bore 29 of sleeve 23 and lumen 123 of member 115 may be coated with one or more lubricious substances. Also, an anti-microbial coating may be applied to some or all of the outer surfaces of bolster 111 to ward off bacterial infection in the area of the stoma.

It should be noted that, although bolster 111 is disclosed in the present embodiment as being a unitary structure, bolster 111 need not be a unitary structure and may be formed by constructing lower portion 112 and upper portion 113 as separate pieces which are thereafter joined together by suitable means (e.g., adhesives, fasteners, complementary threaded portions, etc.). In fact, lower portion 112 and upper portion 113 may be separately formed and then coupled together in such a manner as to permit upper portion 113 to rotate or swivel on lower portion 112. Alternatively, upper portion 113 could even be utilized in combination with lower portion 112 without actually physically joining upper portion 113 to lower portion 112.

Also, in another embodiment (not shown), upper portion 113 could be replaced in its entirety with a block of silicone having an elbow-shaped (or otherwise bent) channel whose lower end is aligned with bore 29.

Finally, it should be recognized that lower portion 112 could be replaced with other conventional or novel external bolster designs.

Figure 4:
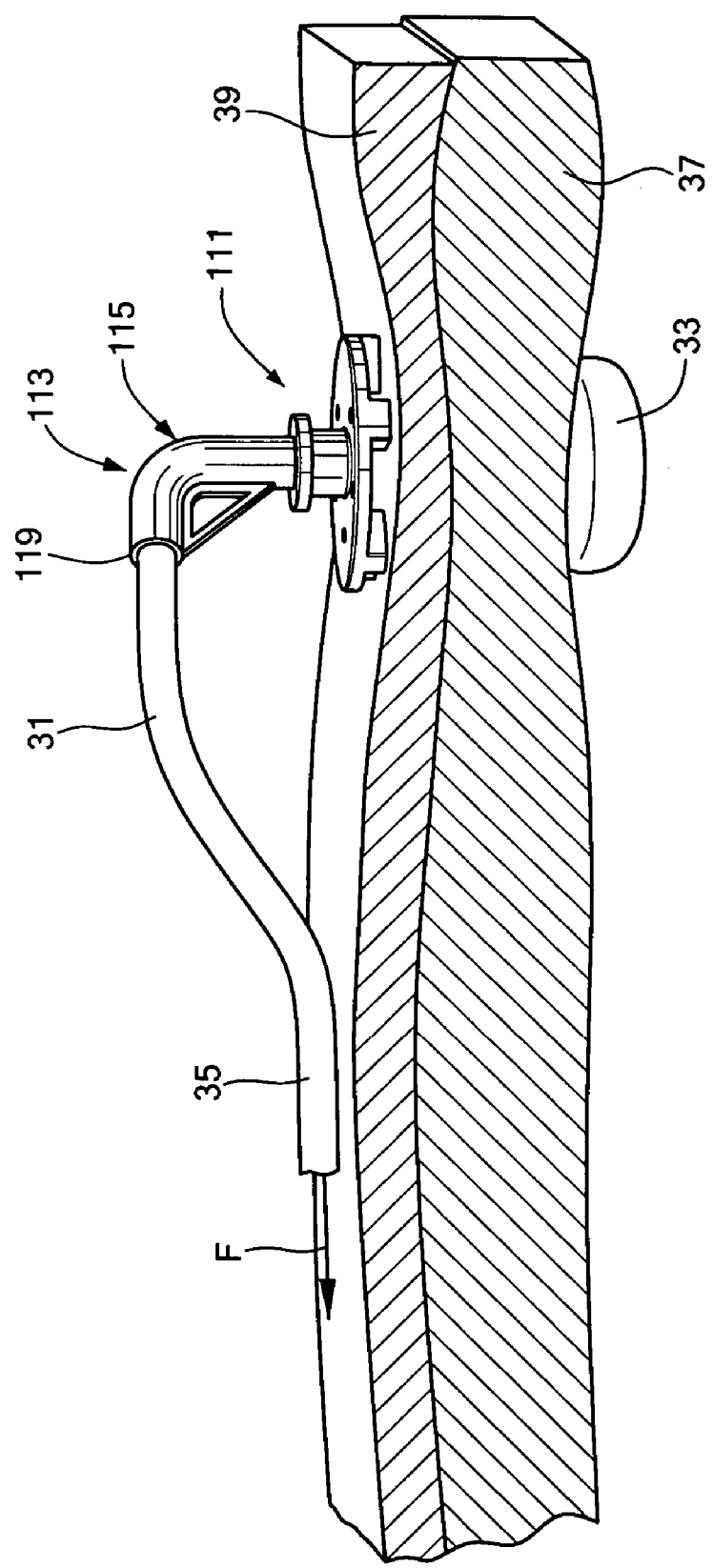
FIG. 4 is a perspective view of the external bolster shown in FIGS. 3(a) and 3(b), the external bolster being shown mounted on a PEG device, the PEG device being shown implanted in the body of a patient, the patient's body being shown in fragmentary section.

Referring now to FIG. 4, external bolster 111 is shown mounted over a PEG device that has been implanted in a patient, the PEG device comprising a tube 31 having an internal end 33 and an external end 35, internal end 33 being in the form of a dome-shaped internal bolster. As can be seen, as a result of the bend in tubular member 115, an externally-directed withdrawal force F applied to external end 35 of tube 31 is directed at approximately a right angle relative to the portion of feeding tube 31 that extends through abdominal wall 39 and stomach wall 37 of the patient. As a result, only a small portion of the withdrawal force is actually transmitted to feeding tube 31 in a direction opposite to the insertion angle of the feeding tube.

As can also be seen in FIG. 4, another desirable aspect of bolster 111 is that, due in part to the height h of tubular member 115, a substantial length of the externally-extending portion of tube 31 is elevated relative to the patient's skin. As a result of keeping this length of tubing away from the patient's skin, the patient is rendered less susceptible to irritation, ulcers and other complications of the type caused by having the feeding tube contact the patient's skin for a prolonged period of time.

Figure 5A:
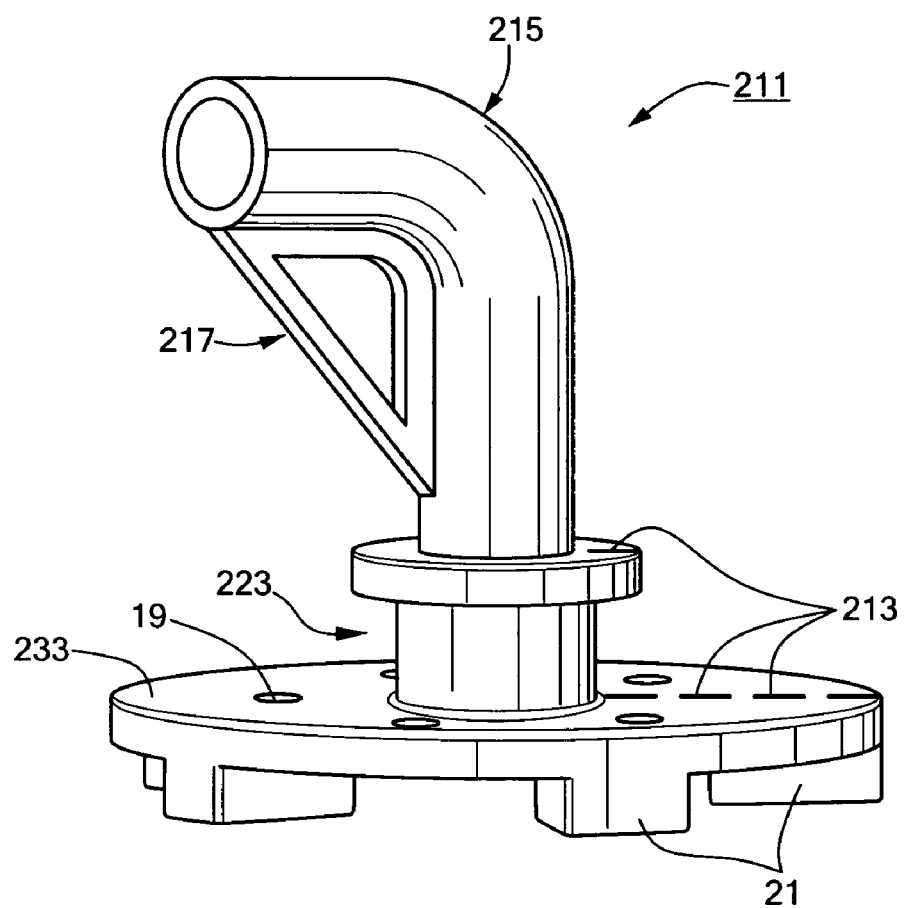
FIGS. 5(a) and 5(b) are perspective and rear views, respectively, of a second embodiment of an external bolster constructed according to the teachings of the present invention.
Figure 5B:
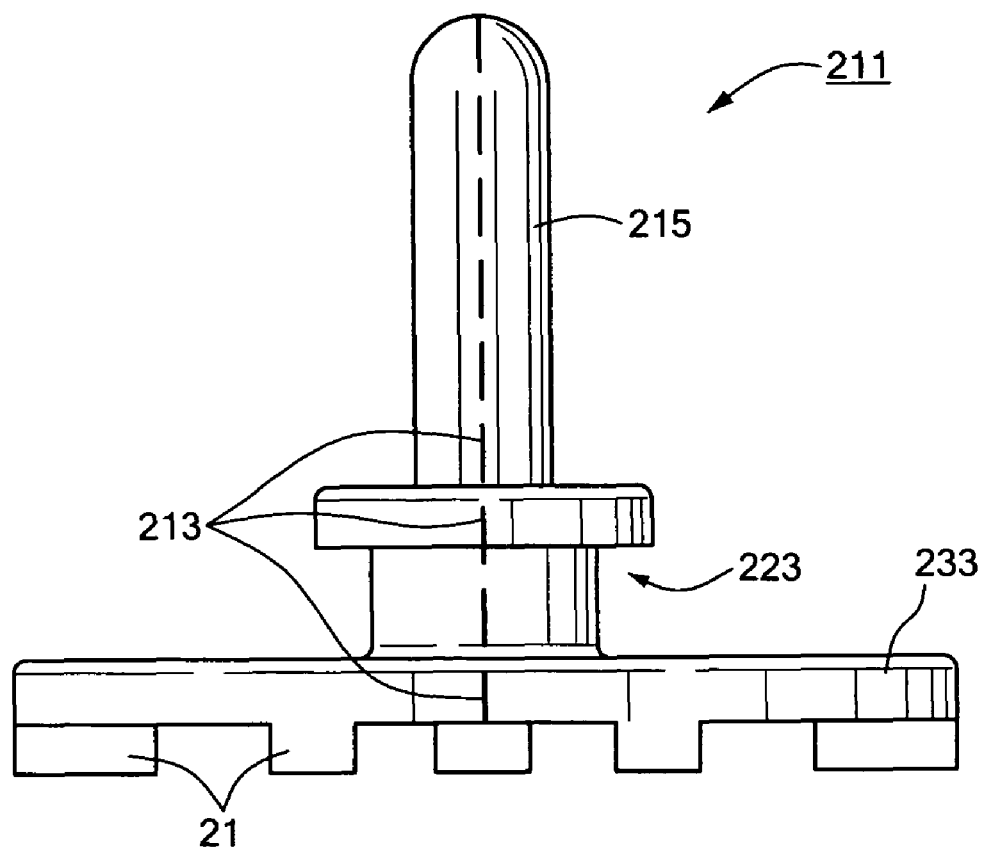

Referring now to FIGS. 5(a) and 5(b), there are shown various views of a second embodiment of an external bolster constructed according to the teachings of the present invention, said external bolster being represented generally by reference numeral 311.

Bolster 211 is similar in most respects to bolster 111, the principal difference between the two bolsters being that bolster 211 includes a series of perforations 213 that extend the respective heights of tubular member 215, sleeve 223 and base 233 and that may be used, when torn, to form a longitudinal slit, said slit facilitating the insertion and removal of a catheter into and out of bolster 211.

Figure 6A:
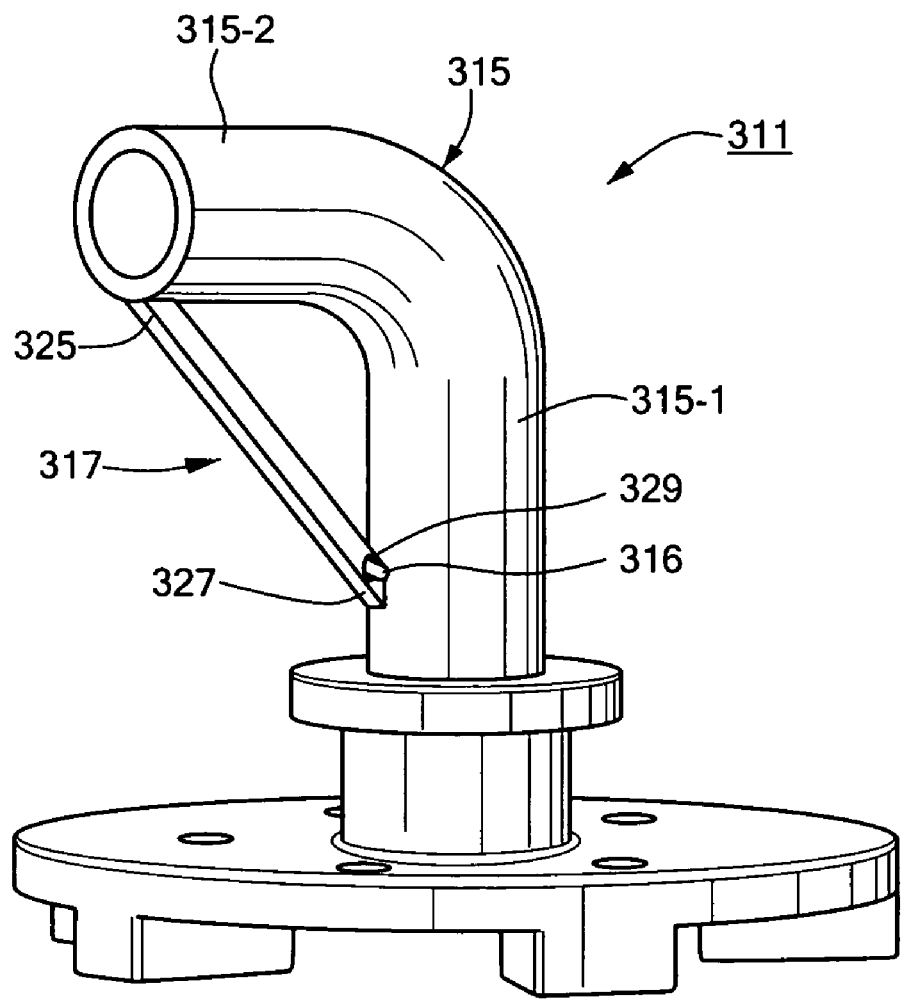
FIGS. 6(a) and 6(b) are perspective views of a third embodiment of an external bolster constructed according to the teachings of the present invention, the external bolster being shown with its tubular strain relief member in a bent state and in a straight state, respectively.
Figure 6B:
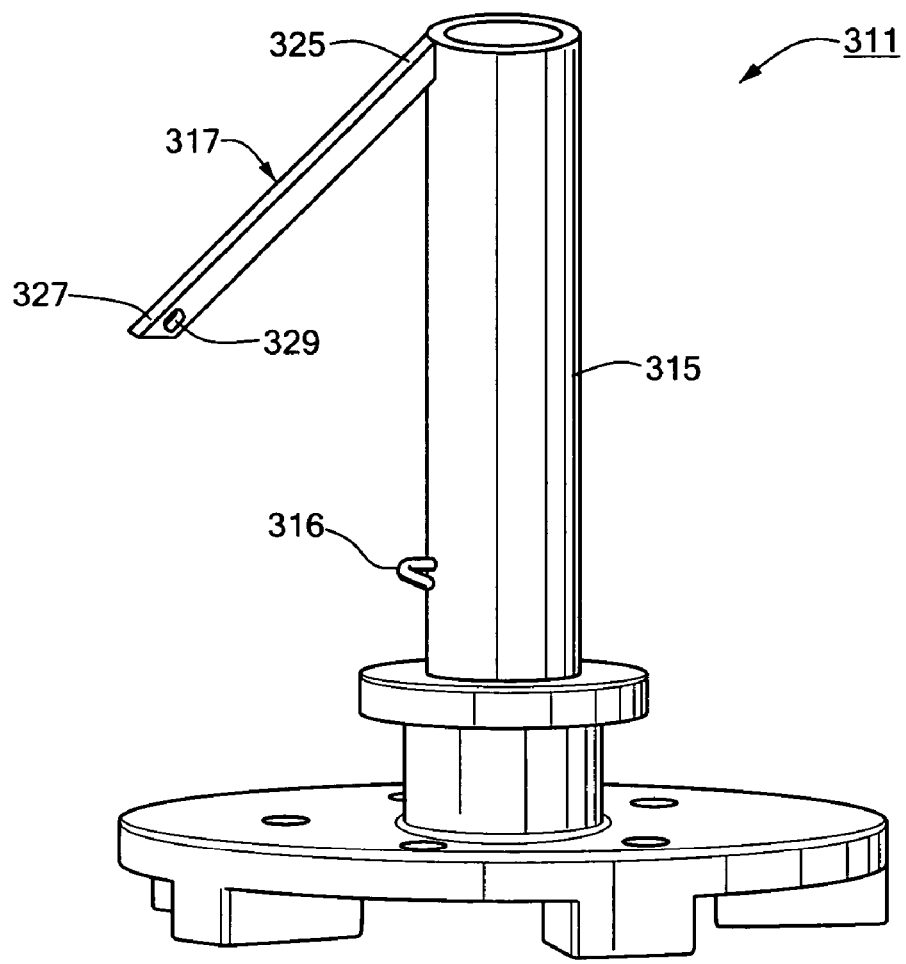

Referring now to FIGS. 6(a) and 6(b), there are shown various views of a third embodiment of an external bolster constructed according to the teachings of the present invention, said external bolster being represented generally by reference numeral 311.

Bolster 311 is similar in most respects to bolster 111, the principal difference between the two bolsters being that bolster 311 includes a tubular member 315 and a tether 317, instead of tubular member 115 and tether 117, respectively. Tubular member 315 differs from tubular member 115 in that tubular member 315 is shaped to include a hooked catch 316 that extends outwardly a short distance from vertical arm 315-1 of member 315. Tether 317 differs from tether 117 in that tether 317 has a first or fixed end 325 that is fixedly secured to the horizontal arm 315-2 of tubular member 315 and a second or free end 327 that includes an opening 329 adapted to receive catch 316 in such a way as to permit second end 327 of tether 317 to be releasably secured to tubular member 315. In this manner, when one wishes to insert a catheter through member 315 or to remove a catheter from member 315, one may first disconnect second end 327 of tether 317 from tubular member 315, thereby permitting tubular member 315 to assume its natural, straight shape. As can be appreciated, insertion of a catheter through the lumen of tubular member 315 or removal of a catheter from the lumen of tubular member 315 is easier when tubular member 315 is straight than when tubular member 315 is bent. After a catheter has been inserted through or removed from member 315, second end 327 of tether 317 may be reconnected to tubular member 315 to return tubular member 315 to its bent state.

It is to be understood that numerous modifications could be made to bolsters 111, 211 and 311 without departing from the spirit of the present invention. For example, although tethers 117, 217 and 317 are designed to provide right angle bends in tubular members 115, 215 and 315, respectively, tethers 117, 217 and 317 could be used to achieve a different angular bend in tubular members 115, 215 and 315, respectively.

For example, the angular bend in tubular members 115, 215 and 315 could be increased to an angle greater than 90° and less than 180°. As can be appreciated, increasing the bend angle of tubular members 115, 215 and 315 above 90° (i) decreases the degree of strain relief provided by the tubular members but (2) increases the degree of separation between the externally-extending portion of the feeding tube and the patient's skin.

Alternatively, the angular bend in tubular members 115, 215 and 315 could be decreased to an angle greater than 0° and less than 90°. As can be appreciated, decreasing the bend angle of tubular members 115, 215 and 315 below 90° (i) increases the degree of strain relief provided by the tubular members but (2) decreases the degree of separation between the externally-extending portion of the feeding tube and the patient's skin.

Moreover, whereas tethers 117, 217 and 317 have been described above as being integrally formed with tubular members 115, 215 and 315, respectively, one could replace tethers 117, 217 and 317 with filaments, threads or the like, one or both ends of which are bonded or insert-molded to tubular members 115, 215 and 315. Furthermore, one could reinforce the bend in tubular members 115, 215 and 315 with a braid, a bent rod, a spring, an oversleeve or co-extruded tough material.

The embodiments of the present invention described above are intended to be merely exemplary and those skilled in the art shall be able to make numerous variations and modifications to them without departing from the spirit of the present invention. All such variations and modifications are intended to be within the scope of the present invention as defined in the appended claims.

What is claimed is:

1. An external bolster for a medical catheter implanted in a patient at an insertion site, said external bolster comprising:
   (a) a base, said base being enlarged relative to the insertion site of the medical catheter, said base having an opening through which the medical catheter may be inserted;
   (b) a strain relief member, said strain relief member being coupled to said base and through which the medical catheter may be inserted, said strain relief member comprising a tube having a first end distal to said base, a second end proximal to said base, and a longitudinal lumen extending from said first end of said tube to said second end of said tube, said strain relief member further comprising a hook positioned on the exterior of said tube proximate to said second end of said tube; and
   (c) a tether, said tether having a first end and a second end, said first end of said tether being secured to said tube at a point proximate to said first end of said tube, said second end of said tether comprising an opening through which said hook is removably received to maintain the tube in a bent shape, so that said tube is reversibly transformable between the bent shape comprising first and second arms positioned relative to one another at an angle greater than 0 degrees and less than 180 degrees and a straight shape comprising a single arm, wherein said tube, when in said bent shape, causes the medical catheter to assume a bent shape and, when in said straight shape, causes the medical catheter to assume a straight shape.

2. The external bolster as claimed in claim 1 wherein said first arm and said second arm are positioned relative to one another in said bent shape at an angle of approximately 90 degrees.

3. The external bolster as claimed in claim 1 wherein said second arm has an end aligned coaxially with said opening of said base.

4. The external bolster as claimed in claim 1 wherein said tether and said strain relief member form a unitary structure.

5. The external bolster as claimed in claim 1 wherein said strain relief member is made of a flexible material.

6. The external bolster as claimed in claim 1 wherein said base has a top surface and a bottom surface, said external bolster further comprising means extending downwardly from said bottom surface of said base for elevating said base relative to the patient.

7. The external bolster as claimed in claim 1 wherein said base is shaped to include a plurality of transverse air holes.

8. The external bolster as claimed in claim 1 wherein said base has a top surface, said external bolster further comprising a sleeve extending upwardly from said top surface, said sleeve being aligned with said opening in said base and jointly defining a central bore, said sleeve having a top end, said second end of said tube being coaxially disposed on said top end of said sleeve.

9. The external bolster as claimed in claim 8 wherein said strain relief member has a height of about 1-2 inches.

10. The external bolster as claimed in claim 8 wherein each of said central bore and said longitudinal lumen is dimensioned for an interference fit with the medical catheter.

11. The external bolster as claimed in claim 1 wherein said strain relief member is fixed relative to said base.

12. The external bolster as claimed in claim 1 wherein said second end of said tube is coaxially aligned with the opening in said base, said external bolster further comprising means for elevating said base relative to the patient to promote the circulation of air under said base.

13. The external bolster as claimed in claim 12 wherein said angle is approximately 90 degrees.

14. The external bolster as claimed in claim 12 wherein said base, said elevating means, said strain relief member and said tether form a unitary structure.

15. The combination of:
(a) a medical catheter, said medical catheter including a first end, a second end, and a longitudinal lumen; and
(b) an external bolster for the medical catheter, said external bolster comprising:
(1) a base, said base being enlarged relative to the insertion site of the medical catheter, said base having an opening through which the medical catheter is inserted;
(2) a strain relief device coupled to said base, said strain relief device comprising a flexible tubular member including a first arm terminating in a first end distal to said base, a second arm terminating in a second end proximal to said base, and a longitudinal lumen extending from said first end of said tubular member to said second end of said tubular member, said first arm and said second arm being disposed relative to one another at an angle greater than 0 degrees and less than 180 degrees, said medical catheter being inserted into said strain relief device, with said first end of said medical catheter extending beyond said first end of said first arm and said second end of said medical catheter extending beyond said second end of said second arm, said strain relief device further comprising a hook positioned on the exterior of said tubular member proximate to said second end of said tubular member; and
(3) a tether, said tether having a first end and a second end, said first end of said tether being secured to said tubular member at a point proximate to said first end of said tubular member, said second end of said tether comprising an opening through which said hook is removably received to maintain the tubular member in a bent shape, so that said tubular member is reversibly transformable between the bent shape comprising first and second arms positioned relative to one another at an angle greater than 0 degrees and less than 180 degrees and a straight shape, wherein said tubular member, when in said bent shape, causes the medical catheter to assume a bent shape and, when in said straight shape, causes the medical catheter to assume a straight shape.

16. The combination of claim 15 wherein said medical catheter is a feeding tube, an internal bolster being disposed at said second end of said medical catheter.

17. The combination as claimed in claim 15 wherein said strain relief device is dimensioned to provide an interference fit with said medical catheter.

18. The combination as claimed in claim 15 wherein said first arm and said second arm of said flexible tubular member are disposed relative to one another at an approximate right angle.

19. The combination as claimed in claim 15 wherein said strain relief device and said external bolster form a unitary structure.

20. The combination as claimed in claim 15 wherein said base is shaped to define a plurality of air holes, each air hole extending through said base from its top surface to its bottom surface.

21. The combination as claimed in claim 15 wherein said external bolster further includes a plurality of feet which extend downwardly from the bottom surface of said base in a spaced apart relationship.

22. An external bolster for a medical catheter implanted in a patient at an insertion site, said external bolster comprising:
(a) a base, said base being enlarged relative to the insertion site of the medical catheter, said base having an opening through which the medical catheter may be inserted; and
(b) a strain relief member, said strain relief member being coupled to said base, said strain relief member comprising a tube having a longitudinal lumen through which the medical catheter may be inserted, said strain relief member further including a catch positioned on the exterior of said tube; and
(c) a tether, said tether having a first end and a second end, said first end of said tether having means for releasably engaging said catch to maintain the tube in a bent shape, so that said tube is transformable between the bent shape comprising first and second arms positioned relative to one another at an angle greater than 0 degrees and less than 180 degrees and a straight shape comprising a single arm, wherein said tube, when in said bent shape, causes the medical catheter to assume a bent shape and when in said straight shape, causes the medical catheter to assume a straight shape.

23. An external bolster for a medical catheter implanted in a patient at an insertion site, said external bolster comprising:
(a) a base, said base being enlarged relative to the insertion site of the medical catheter, said base having an opening through which the medical catheter may be inserted;
(b) a strain relief member, said strain relief member being coupled to said base and through which the medical catheter may be inserted, said strain relief member comprising a tube having a first end distal to said base, a second end proximal to said base, and a longitudinal lumen extending from said first end of said tube to said second end of said tube, said strain relief member further comprising a hook positioned on the exterior of said tube; and
(c) a tether, said tether having a fixed end and a free end, said fixed end of said tether being fixedly secured to said tube, said free end of said tether having an opening through which said hook is removably received so that, when said hook is received within said opening and, thus, said free end of said tether is secured to said tube, said tube assumes a bent shape comprising first and second arms positioned relative to one another at an angle greater than 0 degrees and less than 180 degrees, and so that, when said hook is not received within said opening and, thus, said free end of said tether is not secured to said tube, said tube assumes a straight shape comprising a single arm.

24. The external bolster as claimed in claim 22 wherein said catch is a hook and wherein said means for releasably engaging said catch comprises an opening in said tether through which said catch is removably received.

* * * * *